United States Patent

Matsuda et al.

[11] Patent Number: 5,672,783
[45] Date of Patent: Sep. 30, 1997

[54] METHOD FOR PRODUCING 3,7-DIMETHYL-5,7-OCTADIENE-1-OL OR ROSE OXIDE

[75] Inventors: Hiroyuki Matsuda, Kanagawa; Takeshi Yamamoto, Tokyo, both of Japan

[73] Assignee: Takasago International Corporation, Tokyo, Japan

[21] Appl. No.: 705,205

[22] Filed: Aug. 29, 1996

[30] Foreign Application Priority Data

Aug. 29, 1995 [JP] Japan ................................ 7-242393

[51] Int. Cl.$^6$ .................................................. C07C 29/60
[52] U.S. Cl. ........................................... 568/903; 549/356
[58] Field of Search ................................ 568/903, 876; 585/529, 520, 611, 639, 607; 549/356

[56] References Cited

U.S. PATENT DOCUMENTS 4,312,717  1/1982  Suzukamo et al. ................. 204/59 R
4,340,544  7/1982  Suzukamo et al. ..................... 549/356

FOREIGN PATENT DOCUMENTS 0021769   7/1981  European Pat. Off. .
62033134  6/1985  Japan .

*Primary Examiner*—C. Warren Ivy
*Assistant Examiner*—Charanjit S. Aulakh
*Attorney, Agent, or Firm*—Sughrue, Mion, Zinn, Macpeak and Seas

[57] ABSTRACT

Simple methods for producing 3,7-dimethyl-5,7-octadiene-1-ol and rose oxide are disclosed. Each of the methods comprises only one step in which the raw material, 3,7-dimethyl-6-hydroxy-7-octene-1-ol is dehydrated or further cyclized by heating while stirring at 80° to 160° C. in the presence of a zero-valent or divalent phosphine-palladium complex, or a combination of zero-valent or divalent palladium and a phosphorous compound having coordinating capabilities such as the combination of palladium acetate and triphenylphosphine. The methods give high yields and have cost saving characteristics.

4 Claims, No Drawings

METHOD FOR PRODUCING 3,7-DIMETHYL-5,7-OCTADIENE-1-OL OR ROSE OXIDE

BACK GROUND OF THE INVENTION

1. Field of the Invention

The present invention relates to a novel method for producing rose oxide, which is an aromatic component of rose oils and geranium oils, and also relates to that for producing an intermediate for synthesizing rose oxide.

2. Description of the Related Arts

Methods for producing 3,7-dimethyl-5,7-octadiene-1-ol, which is an important intermediate for synthesizing rose oxide, have been publicly known before the filing date of the present application as disclosed in, for example, the Japanese Patent Publication No. 45-5525 and the Japanese Laid-open Patent Publication No. 62-33134. In these Publications, 3,7-dimethyl-5,7-octadiene-1-ol is produced according to the below-described reaction formula.

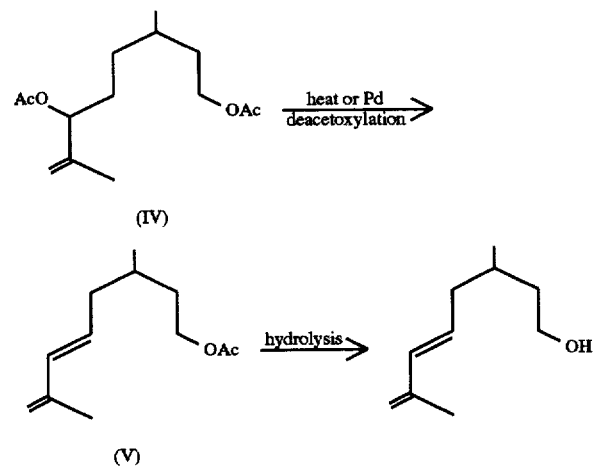

Specifically, 3,7-dimethyl-1-acetoxy-5,7-octadiene (Chemical Formula V of the above-described reaction formula) is obtained from 3,7-dimethyl-1,6-diacetoxy-7-octene (IV) by thermal decomposition or deacetoxylation catalyzed with a palladium complex, and subsequently, the acetic ester thus obtained is hydrolyzed to produce 3,7-dimethyl-5,7-octadiene-1-ol.

This procedure has been, however, disadvantageous because many byproducts such as a compound having cis double bond, position or stereo-isomers of the diene are simultaneously produced other than the compound having trans double bond.

No suitable method for dehydrating 3,7-dimethyl-6-hydroxy-7-octene-1-ol (below described Chemical Formula I) directly into 3,7-dimethyl-5,7-octadiene-1-ol has yet been found. Further, only a few examples of heat reaction methods using acid catalysts have been reported as to one-step conversion, which comprises dehydration and subsequent cyclization reaction, of 3,7-dimethyl-6-hydroxy-7-octene-1-ol (I) into rose oxide (III). The rose oxide products obtained by such methods are mixtures containing compounds which have low boiling points, isomers which have complicated structures and others besides the desired rose oxide (III). Therefore, such products are unsatisfactory in all view points of yield, purity, and aroma.

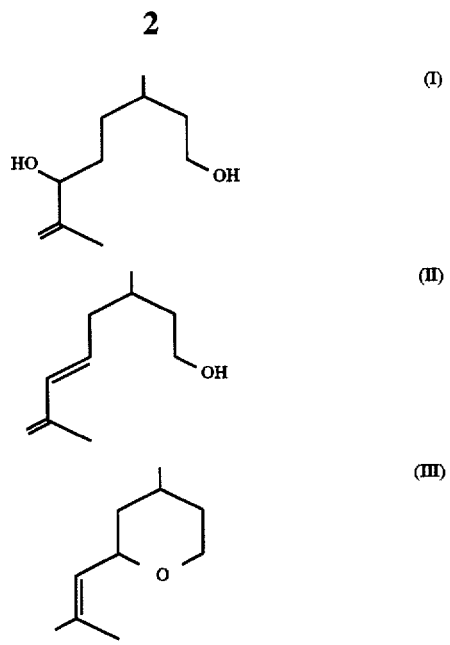

SUMMARY OF THE INVENTION

In view of the above, it has been desired to establish a method for selectively producing 3,7-dimethyl-5,7-octadiene-1-ol, which is an important intermediate for producing rose oxide, by directly dehydrating 3,7-dimethyl-6-hydroxy-7-octene-1-ol (I), and to establish a simple method for producing rose oxide by progressing cyclization subsequent to dehydration under the same reaction conditions, the method comprising one step, giving a higher yield and a high level of purity of the product which cannot be achieved by methods using conventional conditions for acid catalysis. Particularly, it has been desired to develop a method by which the above-mentioned requirements can be satisfied and by which compounds having trans double bond can be obtained in relatively high contents. Accordingly, the object of the present invention is to provide such a method.

Under the above-mentioned circumstances, the Inventors have earnestly investigated and developed a practical process for producing rose oxide (III) which has a high level of purity. In the process, such rose oxide (III) can be obtained by a direct dehydration and cyclization of 3,7-dimethyl-6-hydroxy-7-octene-1-ol (I) in the presence of a zero-valent or divalent palladium complex, namely, by progressing reactions not under the conventional acidic and high temperature conditions using an acid catalyst, which causes production of byproducts, but under conditions close to neutrality. In the course of achieving the present invention, the Inventors have further found that either of the dehydrated product, i.e. 3,7-dimethyl-5,7-octadiene-1-ol, or the cyclized product, i.e. rose oxide (III) can be obtained as the predominant product by selecting the phosphine ligand of the zero-valent or divalent phosphine-palladium complex.

Accordingly, an aspect of the present invention is a method for producing 3,7-dimethyl-5,7-octadiene-1-ol having the chemical formula:

characterized in that 3,7-dimethyl-6-hydroxy-7-octene-1-ol having the chemical formula:

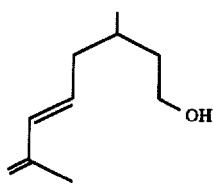
(II)

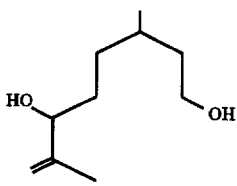
(I)

is dehydrated in the presence of a zero-valent or divalent phosphine-palladium complex.

Further, another aspect of the present invention is a method for producing rose oxide having the chemical formula:

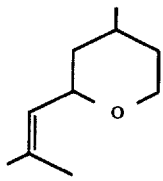
(III)

characterized in that 3,7-dimethyl-6-hydroxy-7-octene-1-ol having the chemical formula:

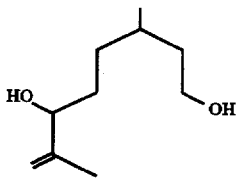
(I)

is dehydrated and cyclized in the presence of a zero-valent or divalent phosphine-palladium complex.

DESCRIPTION OF THE PREFERRED EMBODIMENTS

The starting material in the present invention, 3,7-dimethyl-6-hydroxy-7-octene-1-ol (I) may be prepared by publicly known methods expressed by the below-described chemical equation (c.f. the Japanese Laid-open Patent Publication No. 52-93706).

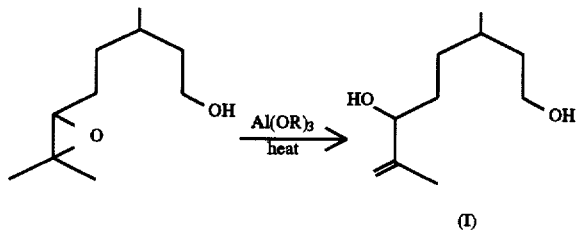
(I)

Zero-valent or divalent phosphine-palladium complexes (hereinafter, may be referred to simply as "palladium complexes") are used for dehydration and cyclization of thus obtained 3,7-dimethyl-6-hydroxy-7-octene-1-ol (I) according to the method of the present invention.

Among palladium complexes to be used in the present invention, zero-valent palladium complexes are publicly known and commercially available as, for example, tetrakis (triphenylphosphine)palladium(0) and so forth. In such a palladium complex, palladium itself is neutral in its electrical charge, and there are basically 4 coordinate bonds. The characteristics of the reaction site around palladium, which is to be an active species, can be varied by properly selecting the type of the ligand, and Lewis acidity, as exhibited by bivalent palladium having a positive charge, is considered to be substantially absent. Also, divalent palladium complexes are publicly known and commercially available as, for example, bis(benzonitrile)palladium(II) chloride and so forth. In such a palladium complex, palladium itself has a positive divalent electric charge, and there are basically 2 ionic bonds and 2 coordinate bonds.

In the present invention, the above-mentioned commercially available complexes may be used as the zero-valent or divalent palladium complex. Further, in situ production of zero-valent or divalent palladium complex may be adopted, wherein a zero-valent or divalent palladium compound and a phosphorous compound having coordinating capabilities are introduced in the reaction mixture. Alternatively, the zero-valent or divalent palladium complex may be prepared beforehand.

Examples of the compound for preparing a zero-valent palladium complex may include organometal compounds containing palladium such as palladium(II) acetate, palladium(II) acetylacetonate, or palladium(0) bis (dibenzylideneacetone). Meanwhile, examples of the compound for preparing a divalent palladium complex may include palladium(II) chloride, bis(triphenylphosphine)palladium(II) chloride, and others. Further, examples of the phosphorous compound may include triphenylphosphine, tributylphosphine, 1,2-diphenylphosphinoethane, 1,3-diphenylphosphinopropane, 1,4-diphenylphosphinobutane, and bidenate ligand such as 2,2'-bis(diphenylphosphino)-1, 1'-binaphthyl(BINAP), 2,2'-bis(di-p-tolylphosphino)-1,1'-binaphthyl, 2,2'-bis(diphenylphosphino)-6,6'-dimethyl-1,1'-biphenyl, 2,3-bis(di-p-tolylphosphino)butane or 2,2'-bis(dicyclohexylhosphino)-6,6'-dimethyl-1,1'-binaphthyl.

According to the present invention, the amount of the above-described zero-valent or divalent palladium complex to be used should preferably be about 0.0001 to 1 mol %, more preferably, about 0.01 to 0.1 mol % relative to the substrate (I). With less than about 0.0001 mol % of a palladium complex catalyst, the rate of reaction becomes slow. Meanwhile, a catalyst exceeding about 1 mol % does not bring any additional effect, but merely costs more. Together with the palladium complex, it is preferred to use the above-mentioned phosphorous compound having coordinating capabilities in an amount of about 2 to 20 times moles relative to the palladium complex catalyst. The existence of such a phosphorous compound elongates the duration of the catalyst activity.

As an unique feature of the present invention, whether 3,7-dimethyl-5,7-octadiene-1-ol (II) should be produced by the procedure up to dehydration or rose oxide (III) should be produced by further carrying out cyclization can be controlled by selecting the phosphorous compound to be used which has coordinating capabilities. Specifically, the dehydrate will be the predominant product when an unidentate ligand such as triphenylphosphine is used. On the other hand, when a bidentate ligand such as 1,4-diphenylphosphinobutane is used, cyclization will successively progress, and therefore, rose oxide will be the predominant product. Further, 3,7-dimethyl-5,7-octadiene-1-ol (II) can be selectively obtained by continuously distilling out of the system the dehydrate produced in the reaction system.

The reactions according to the present invention, namely, the reactions for producing 3,7-dimethyl-5,7-octadiene-1-ol (II) by dehydration of 3,7-dimethyl-6-hydroxy-7-octene-1-ol (I), or rose oxide by dehydration and subsequent cyclization of the same will progress by heating in the presence of the above-described palladium complex catalyst which is provided with a catalytic activity to be exhibited in the presence or absence of a solvent.

As the solvent, polar solvents such as alcoholic solvents, hydrocarbon solvents, DMF, and others, or mixed solvents thereof can be used. The practical examples which are particularly effective may include butanol, hexanol, cumene, xylene, and others. The concentration of the substrate (I) in the solvent should preferably be 0.5 to 40% by weight, and more preferably 1 to 20% by weight. The reaction can be carried out at a temperature of 80° to 160° C., preferably 100° to 150° C. At a temperature below 80° C., the rate of reaction becomes slow. On the other hand, at a temperature exceeding 160° C., byproducts are easily produced since decomposition of the palladium complex occurs.

Though the reaction is usually carried out at atmospheric pressure, it may be performed under reduced pressure when no solvent is used. In such a case, it is preferred to reduce the pressure to about 10 to 50 mmHg and to distill the dehydrated product out of the reaction system.

The present invention will be further illustrated with the following examples, which are not directed to limiting the scope of the present invention.

EXAMPLE 1

Production of 3,7-dimethyl-5,7-octadiene-1-ol (II) by Dehydration of 3,7-dimethyl-6-hydroxy-7-octene-1-ol (I)

(S)-3,7-dimethyl-6-hydroxy-7-octene-1-ol (I) (10.0 g, 58.1 mmol), palladium acetate (130.0 mg, 0.579 mmol), and triphenylphosphine (1.52 g, 5.795 mmol) were placed in a 50 ml three neck distillation flask provided with a thermometer and a vacuum distilling apparatus having a side arm. Butanol (20 ml) was then added to the flask and the mixture was heated for 12 hours with stirring at a reaction temperature of 115° to 120° C. and a atmospheric pressure in a stream of nitrogen. After the reaction had terminated, the flask was evacuated to remove solvent from the reaction mixture, and the resultant was distilled to obtain 7.2 g (89° to 91° C./4 mmHg) of (S)-3,7-dimethyl-5,7-octadiene-1-ol (II). The yield was 80%.

EXAMPLE 2

Production of 3,7-dimethyl-5,7-octadiene-1-ol (II) by Dehydration of 3,7-dimethyl-6-hydroxy-7-octene-1-ol (I)

(S)-3,7-dimethyl-6-hydroxy-7-octene-1-ol (I) (10.0 g, 58.1 mmol), bis(triphenylphosphine) palladium chloride (40.8 mg, 0.058 mmol), and 1,4-bisphenylphosphinobutane (1.24 g, 2.91 mmol) were placed in a 50 ml three neck distillation flask provided with a thermometer and a vacuum distilling apparatus having a side arm. The mixture was then heated for 6 hours with stirring at a reaction temperature of 150° C. under a reduced pressure of 25 mmHg while distilling dienes which is to be produced. 7.3 g (115° to 120° C./25 mmHg) of (S)-3,7-dimethyl-5,7-octadiene-1-ol (II) was obtained in 82% yield.

EXAMPLE 3

Production of Rose Oxide (III) by Dehydration and Cyclization of 3,7-dimethyl-6-hydroxy-7-octene-1-ol (I)

(S)-3,7-dimethyl-6-hydroxy-7-octene-1-ol (I) (10.0 g, 58.1 mmol), palladium acetate (130.0 mg, 0.579 mmol), and 1,4-bisphenylphosphinobutane (1.24 g, 2.91 mmol) were placed in a 50 ml three neck distillation flask provided with a thermometer and a vacuum distilling apparatus having a side arm. Butanol (20 ml) was then added to the flask and the mixture was heated for 7 hours with stirring at a reaction temperature of 115° to 120° C. in a stream of nitrogen. After the reaction had terminated, the flask was evacuated to remove solvent from the reaction mixture, and the resultant was distilled to obtain 6.3 g (77° to 82° C./8 mmHg) of rose oxide (III). The yield was 70% and the cis:trans ratio of the product was 64:36.

EXAMPLE 4

Production of Rose Oxide (III) by Dehydration and Cyclization of 3,7-dimethyl-6-hydroxy-7-octene-1-ol (I)

(S)-3,7-dimethyl-6-hydroxy-7-octene-1-ol (I) (10.0 g, 58.1 mmol), palladium acetate (130.0 mg, 0.579 mmol), and (S)-BINAP (2.26 g, 2.91 mmol) were placed in a 50 ml three neck distillation flask provided with a thermometer and a vacuum distilling apparatus having a side arm. Hexanol (20 ml) was then added to the flask and the mixture was heated for 5 hours with stirring at a reaction temperature of 145° to 150° C. in a stream of nitrogen. After the reaction had terminated, the flask was evacuated to remove solvent from the reaction mixture, and the resultant was distilled to obtain 6.4 g (77° to 82° C./8 mmHg) of rose oxide (III). The yield was 72% and the cis:trans ratio of the product was 52:48.

EXAMPLE 5

Production of Rose Oxide (III) by Dehydration and Cyclization of 3,7-dimethyl-6-hydroxy-7-octene-1-ol (I)

(S) -3,7-dimethyl-6-hydroxy-7-octene-1-ol (I) (10.0 g, 58.1 mmol), palladium chloride (102.7 mg, 0.579 mmol), and (S)-BINAP (2.26 g, 2.91 mmol) were placed in a 50 ml three neck distillation flask provided with a thermometer and a vacuum distilling apparatus having a side arm. Hexanol (20 ml) was then added to the flask and the mixture was heated for 6 hours with stirring at a reaction temperature of 145° to 150° C. in a stream of nitrogen. After the reaction had terminated, the flask was evacuated to remove solvent from the reaction mixture, and the resultant was distilled to obtain 6.3 g (77° to 82° C./8 mmHg) of rose oxide (III). The yield was 70% and the cis:trans ratio of the product was 69:31.

ADVANTAGES OF THE INVENTION

As is obvious from the above description, according to the method of the present invention, a reaction selectively dehydrating the raw material, 3,7-dimethyl-6-hydroxy-7-octene-1-ol (I) dissolved in a solvent or without any solvent is promoted by mere heating in the presence of an extremely small amount of a palladium complex catalyst, by means of which 3,7-dimethyl-5,7-octadiene-1-ol (II) can be produced.

Further, cyclization subsequent to dehydration can also be promoted by varying the types of the phosphorous ligand and/or other reaction conditions, by means of which the objective products of rose oxide (III) can be produced in a high yield of 70% or more. Moreover, the content of the compounds having a trans double bond is high in the product obtained according to the present invention. The present invention, therefore, provides a method which has excellent cost saving characteristics and industrial applicability.

We claim:

1. A method for producing 3,7-dimethyl-5,7-octadiene-1-ol having the chemical formula:

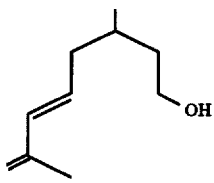
(II)

characterized in that 3,7-dimethyl-6-hydroxy-7-octene-1-ol having the chemical formula:

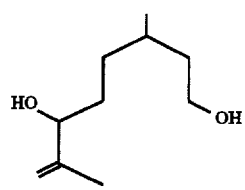
(I)

is dehydrated in the presence of a zero-valent or divalent phosphine-palladium complex.

2. A method for producing 3,7-dimethyl-5,7-octadiene-1-ol according to claim 1, wherein a zero-valent or divalent palladium compound and a phosphorous compound having coordinating capabilities are introduced in the reaction mixture.

3. A method for producing 3,7-dimethyl-5,7-octadiene-1-ol according to claim 1, wherein a content of said zero-valent or divalent palladium phosphine complex ranges from 0.0001 to 1 mol % based on the 3,7-dimethyl-6-hydroxy-7-octene-1-ol.

4. A method for producing rose oxide according to claim 1, wherein a zero-valent or divalent palladium compound and a phosphorous compound having coordinating capabilities are introduced in the reaction mixture.

* * * * *